United States Patent [19]

Sayegh et al.

[11] Patent Number: 5,125,747
[45] Date of Patent: Jun. 30, 1992

[54] OPTICAL ANALYTICAL INSTRUMENT AND METHOD HAVING IMPROVED CALIBRATION

[75] Inventors: Emile Sayegh, Brighton; Eric F. Mooney, Burlington, both of Mass.

[73] Assignee: Tytronics, Inc., Waltham, Mass.

[21] Appl. No.: 596,513

[22] Filed: Oct. 12, 1990

[51] Int. Cl.⁵ .................... G01N 21/31; G01N 21/85; G01J 3/51

[52] U.S. Cl. ................... 356/407; 356/243; 356/410; 356/414; 356/417

[58] Field of Search .............. 356/320, 410, 411, 414, 356/407, 243

[56] References Cited

U.S. PATENT DOCUMENTS

| | | | |
|---|---|---|---|
| 3,734,621 | 5/1973 | Moody et al. | |
| 3,985,441 | 10/1976 | Schoeffel et al. | |
| 4,223,995 | 9/1980 | Fletcher | 356/320 X |
| 4,322,807 | 3/1982 | Chamran et al. | 364/498 |
| 4,323,309 | 4/1982 | Akitomo et al. | 356/319 |
| 4,637,730 | 1/1987 | Ponstingi et al. | 356/411 |
| 4,664,522 | 5/1987 | LeFebre | 356/328 |
| 4,692,883 | 9/1987 | Nelson et al. | 364/571 |
| 4,707,133 | 11/1987 | Roberts et al. | 356/320 |
| 4,786,171 | 11/1988 | LeFebre et al. | 356/326 |
| 4,820,045 | 4/1989 | Boisde et al. | 356/319 |
| 4,838,691 | 6/1989 | Master et al. | 356/319 |
| 4,866,644 | 9/1989 | Shenk et al. | 364/571.02 |
| 4,937,448 | 6/1990 | Mantz et al. | 250/343 |
| 4,947,414 | 9/1990 | Stein | 378/55 |
| 5,020,909 | 6/1991 | Landa | 356/243 X |

FOREIGN PATENT DOCUMENTS 0154323 9/1985 European Pat. Off.
WO90/07697 7/1990 World Int. Prop. O.

OTHER PUBLICATIONS

Liptak et al., "Process Measurement", Instrument Engineers Handbook, pp. 719-722 & 716-717.
Paul E. Mix, "The Design and Application of Process Analyzer Systems", Chemical Analysis, vol. 70, pp. 163-177.
Orion Research, Instruction Manual Model 901 Microprocessor Ionalyzer, 1982, pp. 8-15; Instruction Manual Model 811 Microprocessor pH/Millivolt Meter, p. 11.
Spectral Analytics Corporation, Manual for Model 2000 Process UV Analyzer, 1989, Section IV, pp. 1-2.
"Standard Practice for Describing and Measuring Performance of Dispersive Infrared Spectrophotometers", ASTM Designation: E 932-83, pp. 315-322.
"Standard Practice for Describing and Measuring Performance of Ultraviolet, Visible, and Near Infrared Spectrophotometers", ASTM Designation: E-275-83, 1989, pp. 106-116.
"Standard Practices for General Techniques of Infrared Quantitative Analysis", ASTM Designation: E 168-88, pp. 51-65.
"Standard Practice for General Techniques of Ultraviolet-Visible Quantitative Analysis", ASTM Designation E 169-87, pp. 66-70.

Primary Examiner—Vincent P. McGraw
Attorney, Agent, or Firm—Fish & Richardson

[57] ABSTRACT

Optical analytical instruments to determine a physical parameter of a fluid, and methods of operation of such instruments, are shown. These employ a source of suitable optical radiation, a detector means, means defining a zone for the fluid, means defining an optical path from the radiation source through the fluid zone to the detector means, and reading and control circuitry. At least two readings of optical energy that has been influenced by the fluid are taken without there having occurred substantial change to the fluid. During one of the readings a filter of known absorbance is included in the optical path so that the respective reading represents a calibration reading. A calibration-value-determining means is constructed first to compare, effectively, the two readings to remove the effect of the fluid from the value of the calibration reading, second, to compare, effectively the residual value of the calibration reading to a known value based on the known absorbance of the filter, and, third, on the basis of the second comparison, to make a calibration adjustment based on values derived while the fluid sample remained unchanged in the fluid zone. Novel software implementations of the determinations are shown. Specific examples of instruments and methods implementing these features shown are a dual lamp, no-moving part in-line spectrophotometer, a no-moving part reflection colorimeter capable of on-line or off-line operation, a scatter or fluorescence detecting implementation and a turbidimeter.

43 Claims, 11 Drawing Sheets

$$conc = k\left[\lambda_m - \frac{\lambda_{r_1} + \lambda_{r_2}}{2}\right]$$

OPTICAL ANALYTICAL INSTRUMENT AND METHOD HAVING IMPROVED CALIBRATION

BACKGROUND OF THE INVENTION

The present invention concerns photometers, i.e. optical analytical instruments that employ optical energy to determine physical parameters of fluids such as liquids or gasses found in effluents and in industrial processes.

There are many instances in which it would be useful to have a relatively low cost analytical instrument that could be depended upon to monitor a process or environmental condition at a desired level of accuracy and which did not require highly trained personnel for its operation and maintenance. There is a special need for a low cost instrument in the case of monitoring waste water and effluent gasses before release to the environment. The present invention addresses these needs, and provides general improvements in photometers as well.

SUMMARY OF INVENTION

According to the invention a photometer or optical analytical instrument is provided that is relatively low cost to construct but still has the means to correct its calibration or report the accuracy of its measurements during use, without need for a skilled operator.

Such an instrument is realized according to the invention by means that permit construction with no moving parts, in implementations that are relatively simple, compact, easy to assemble, and requires no alignment.

A principal feature of the invention is an optical analytical instrument capable of producing readings based upon the effect of a beam of optical energy on a fluid to determine a physical parameter of the fluid, the instrument comprising a source of suitable optical radiation, a detector means, means defining a zone for the fluid, means defining an optical path from the radiation source through the fluid zone to the detector means, reading and control circuitry for taking from the detector means at least two readings of optical energy that has been influenced by the fluid without there having occurred substantial change to the fluid, means during one of the readings for including in the optical path a filter of known absorbance so that the respective reading represents a calibration reading, calibration-value-determining means constructed first to compare, effectively, the two readings to remove the effect of the fluid from the value of the calibration reading, second, to compare, effectively the residual value of the calibration reading to a known value based on the known absorbance of the filter, and, third, on the basis of the second comparison, to make a calibration adjustment based on values derived while the fluid sample remained unchanged in the fluid zone.

Preferred embodiments of the aspect of the invention have the following features.

The optical radiation source comprises two separately energizable radiation emitters, the optical path from the source having two branches, one defining a respective optical path from each radiation emitter, with both branches transmitting via a substantially common path through the sample, one of the emitters, denoted the "measure" emitter, energized by the control means during the taking of a normal measurement reading and the other emitter, denoted the "calibration" emitter, energized by the control means during the taking of a calibration reading, the filter of known absorbance being included in the optical path from the calibration emitter to the fluid zone.

The instrument has no moving parts for accomplishing calibration, the control means constructed and arranged such that normal and calibration readings for use by the instrument in establishing the calibration adjustment ar effected by selective energization of the emitters during operation.

The optical analytical instrument is in the form of an in-line analytical instrument in which the means defining the fluid zone comprises a conduit for at least part of a process stream through which process fluid flows, the process stream having a characteristic maximum rate at which the parameter can change, and the reading and control means constructed, in relation to the process stream, to take the two reading within such a short time interval that there is insufficient passage of time to allow substantial change to occur in the parameter of the fluid in the process stream.

The optical analytical instrument is in the form of a titration chamber constructed to be filled by a liquid process stream and, after titration, flushed only by the process stream.

The optical analytical instrument is in the form of a titration chamber constructed to receive a known repeatatable small sample of process stream liquid and after titration said chamber is constructed to be flushed with a suitable liquid.

The optical analytical instrument is in the form of a colorimeter.

The optical analytical instrument is in the form of a colorimeter, the portion of the optical path in the fluid zone being defined by a probe which includes a reflector whereby energy which enters the fluid zone is reflected to pass back through the fluid zone to the detector means.

The optical analytical instrument is in the form of an absorption spectrophotometer, the detector means comprising at least two detectors sensitized to respectively different wavelengths, one wavelength corresponding to a characteristic absorption of a component of interest in the fluid zone, the detected signal varying with the concentration of the component, and the other wavelength being a reference wave-length for which the component of interest has relatively low absorbance.

The optical analytical instrument has the detector means positioned to receive scattered radiant energy from the sample, preferably the filter being positioned to filter the scattered radiant energy and preferably the detector is postioned and adapted to receive Raleigh scattering or fluorescence.

The optical analytical instrument is in the form of a turbidimeter, preferably with an optical reference path bypassing the sample.

Also preferred embodiments of the instrument have the following features.

The means defining the optical path from the radiation source to the fluid zone is comprised of optical fibers.

The means to make a calibration adjustment is constructed to calibrate the instrument, preferably the adjustment comprising means to adjust the sensitivity of the instrument and means to adjust the zero reference of the instrument.

The optical analytical instrument including means to provide the known value in the form of means to store a reading of the detector means taken with the filter of known absorbance in place and with the fluid zone empty.

Another principal feature of the invention is a method of calibrating an optical analytical instrument capable of producing readings based upon the effect of a beam of optical energy on a fluid to determine a physical parameter of the fluid, comprising taking from a detector means at least two readings of optical energy that has been influenced by the fluid in a fluid zone without there having occurred substantial change to the fluid, including in the optical path a filter of known absorbance so that one of the readings represents a calibration reading, first, comparing, effectively, the two readings to remove the effect of the fluid from the value of the calibration reading, second, comparing, effectively, the residual value of the calibration reading to a known value based on the known absorbance of the filter, and, on the basis of the second comparison, making a calibration adjustment based on values derived while the fluid sample remained unchanged in the fluid zone.

Preferred embodiments of this aspect of the invention have the following features.

The optical radiation source comprises two separately energizable radiation emitters, further comprising energizing a "measure" emitter by the control means during the taking of a normal measurement, and energizing a "calibration" emitter, by the control means during the taking of a calibration reading while the filter of known absorbance is included in the optical path from the calibration emitter to the fluid.

The calibration adjustment is effected by selective energization of the emitters during operation without moving any parts of the instrument.

The fluid flows in a process stream further comprising taking two readings by the control means within such a short time interval that there is insufficient passage of time to allow substantial change to occur in the parameter of the fluid in the process stream.

The method includes the steps of filling a titration chamber by a liquid process stream and, after titration, flushing the titration chamber only by the process stream.

The method includes the steps of filling a titration chamber by a liquid process stream and, after titration, flushing the titration chamber by a suitable liquid.

The calibration is performed for a colorimeter, an absorption spectrophotometer, a turbidimeter, or an instrument capable of detecting fluorescence or Raleigh scattering.

The step of making a calibration adjustment calibrates the instrument and preferably adjusts the zero reference of the instrument.

The method includes the step of storing a reading of the detector means taken with the filter of known absorbance in place and with the fluid zone empty.

The step of making a calibration adjustment includes updating a current filter absorbance value.

The calibration adjustment step is periodically repeated and the current filter value is successively updated during these repetitions.

Past trends in the current absorbance value are taken into consideration in updating the current absorbance value.

Another principal feature of the invention is apparatus or method wherein, respectively, the instrument is constructed or the method is conducted to measure concentration or the like, C, according substantially to the relationship:

$$C_{s(n)} = \frac{C_{std} \times (A_{s(n)} - A_2)}{A_F}$$

in which the values are substantially as defined in the following specification.

DESCRIPTION OF THE PREFERRED EMBODIMENTS

Figure 1:
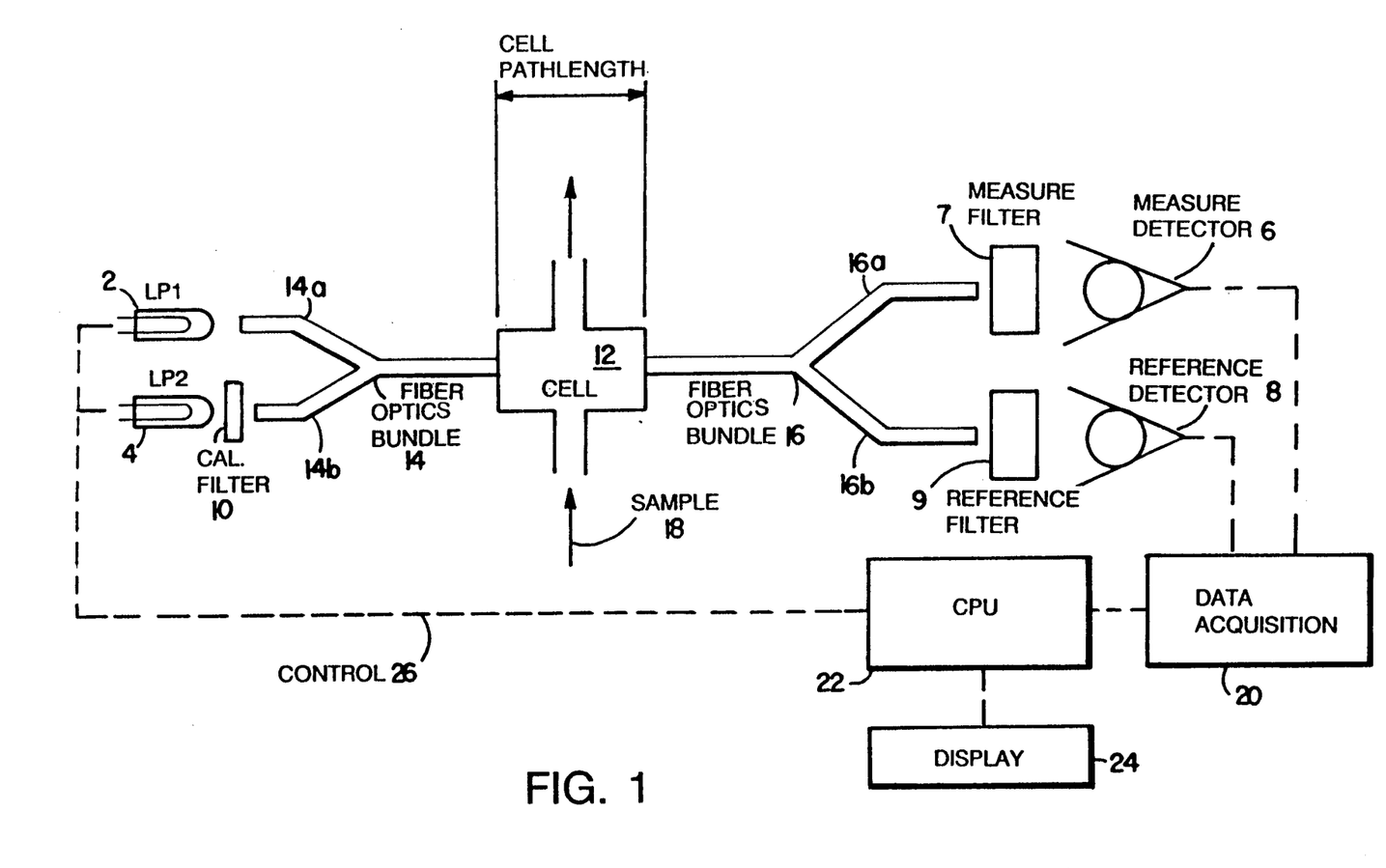
FIG. 1 is a schematic illustration of a dual lamp spectrophotometer that has no moving parts.

Referring to FIG. 1, a dual lamp spectrophotometer for monitoring a continuous flow includes a sample lamp or emitter 2 and a calibration lamp or emitter 4 that are each linked to a central processing unit 22 or other form of calbration-value-determining and control circuitry via a control line 26. The sample and calibration lamps are located in front of respective fiber optic branches 14a and 14b which join to form a random-ordered first fiber optics bundle 14 which provides a common path for energy from the two branches. A calibration filter 10 is disposed between lamp 4 and its fiber optic branch. The calibration filter 10 has a known absorbance at the wavelength to be measured.

The fiber optics bundle leads to a sample cell 12 or other zone for confining a sample 18. Also adjacent to the sample cell, behind the first fiber optics bundle, is a second fiber optics bundle 16 which provides a common path for energy transmitted through the cell. This second fiber optics bundle is split into branches 16a and 16b to provide optical paths through a measure filter 7 and a reference filter 9.

A measure detector 6 and a reference detector 8 are placed behind the measure and reference filters, respectively. The outputs of these detectors are connected to a data acquisition module 20 that is, in turn, connected to the central processing unit 22. A display 24 is also connected to the central processing unit.

The lamps or emitters are capable of emitting optical radiation at a wavelength that is absorbed (or, in other embodiments, otherwise influenced) by the substance to be detected or monitored, where "optical" radiation is defined, for the purposes of this application, as radiation in the visible, infrared and ultraviolet regions of the spectrum.

In operation, a continuous flow of a sample fluid passes through the cell, which acts as conduit for at least a part of a process stream. Alternatively, the cell may be filled with a static sample of a fluid which may be replaced from time to time. The former of these methods enables the instrument to be used, e.g., in in-line monitoring of waste water or industrial processes in which the fluid flows steadily through the cell. The latter enables the instrument to be used, e.g., in on-line monitoring, in which fluid is repeatedly drawn from the process line and used to provide samples, e.g., for titration or colorimetric measurement, and to provide the flushing medium.

An instrument with which present invention is useful is shown in U.S. Pat. Nos. 4,911,891 and 4,910,151 hereby incorporated by reference, both entitled "Sample Monitoring Instrument for On-Line Application".

There are two types of operations that may be performed with this apparatus; "measure" operations and "calibration" operations. The first step in a measure operation is for the central processing unit 22 to cause the sample lamp 2 to illuminate. The sample lamp emits polychromatic light that passes from branch 14a through the first fiber optics bundle 14 and into the cell. In the cell, the light interacts with the sample and certain characteristic wavelengths of the light are absorbed by the constituent materials in the sample.

Figure 2:
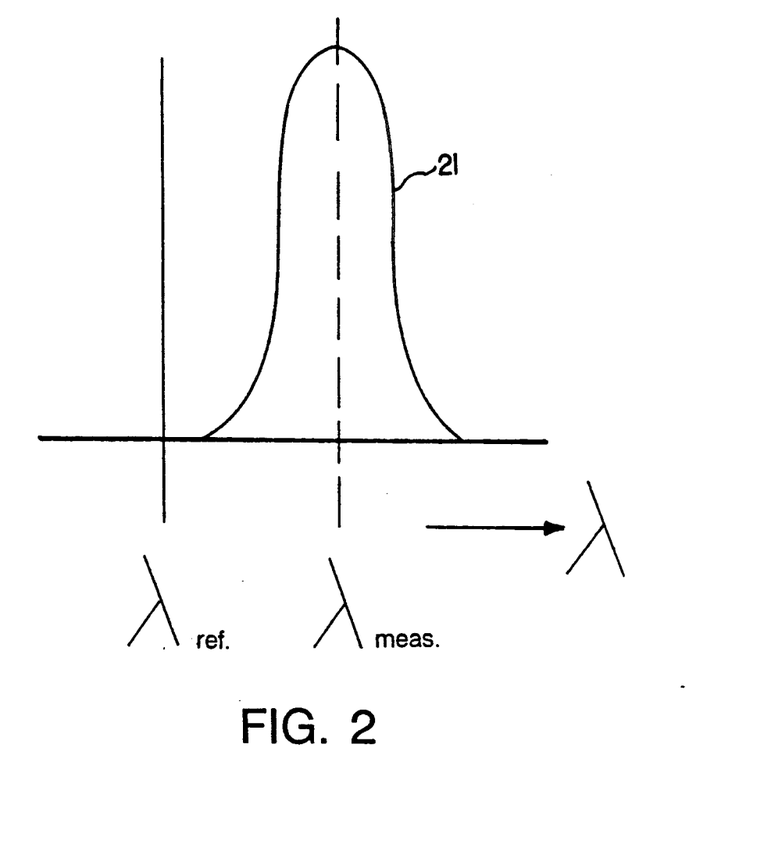
FIG. 2 is a plot of absorbance against wavelength in the spectral region of interest for a sample to be measured.

A portion of the unabsorbed light passes along the common path through the cell into the second fiber optics bundle 16 and exits the bundle in two beams. The first beam passes through a measure filter 7 that attenuates all wavelengths except that of the spectral line of interest for the material being monitored in the spectrophotometer. The spectral line typically corresponds to a characteristic absorption of the compound to be measured. The second beam passes through a reference filter 9 that attenuates all wavelengths except for a reference wavelength that is generally close to the measured wavelength but which does not correspond to a characteristic absorption line of the compound of interest. The relationship between the wavelength at the spectral line of interest and the reference wavelength are shown in FIG. 2. By using the two wavelengths in this manner, the effect of the illumination level of the lamps may be eliminated by performing a differential measurement using two detectors.

These measure and reference detectors 6, 8 detect the light passing through the measure and reference filters, respectively. Each of these detectors produces an electrical signal that has a magnitude related to the amount of light incident upon it and provides that signal to a data acquisition module 20. The response of the sample 18 to the measure wavelength may be determined by $$A = \log_{10} \frac{V_r}{V_m}$$

where A is the absorbance of the sample, $V_m$ is the voltage of the measure detector 6 and $V_r$ is the voltage on reference detector 8. The data acquisition module digitizes the voltage signals from the detectors and provides the digital values to the CPU for processing.

In normal "measure" operation the instrument provides readings for the substance of interest in the sample in the units desired by the user. Typically the reading for a sample is in terms of concentration, $C_s$, for example, percent or ppm. The concentration $C_{s(n)}$ of sample at time n is implemented in the present embodiment according to the relationship:

$$C_{s(n)} = \frac{C_{std} \times (A_{s(n)} - A_z)}{A_F}$$

where:

$C_{s(n)}$ = calculated nth sample concentration, $C_{std}$ = concentration value corresponding to the known absorbance of the filter selected, $A_{s(n)}$ = measured absorbance value with nth sample in situ $A_z$ = previously measured and stored zero absorbance value $A_F$ = previously measured and stored filter absorbance value, all will be explained below. It will be observed that the above equation normalizes the sample concentration to the corresponding ratio of $C_{s+d}$ (the concentration represented by the absorbance of the filter) vs. the measured calibration filter absorbance value $A_F$, thus taking advantage of updates as to any detected drift of the instrument that have been determined by prior calibration readings.

Figure 4:
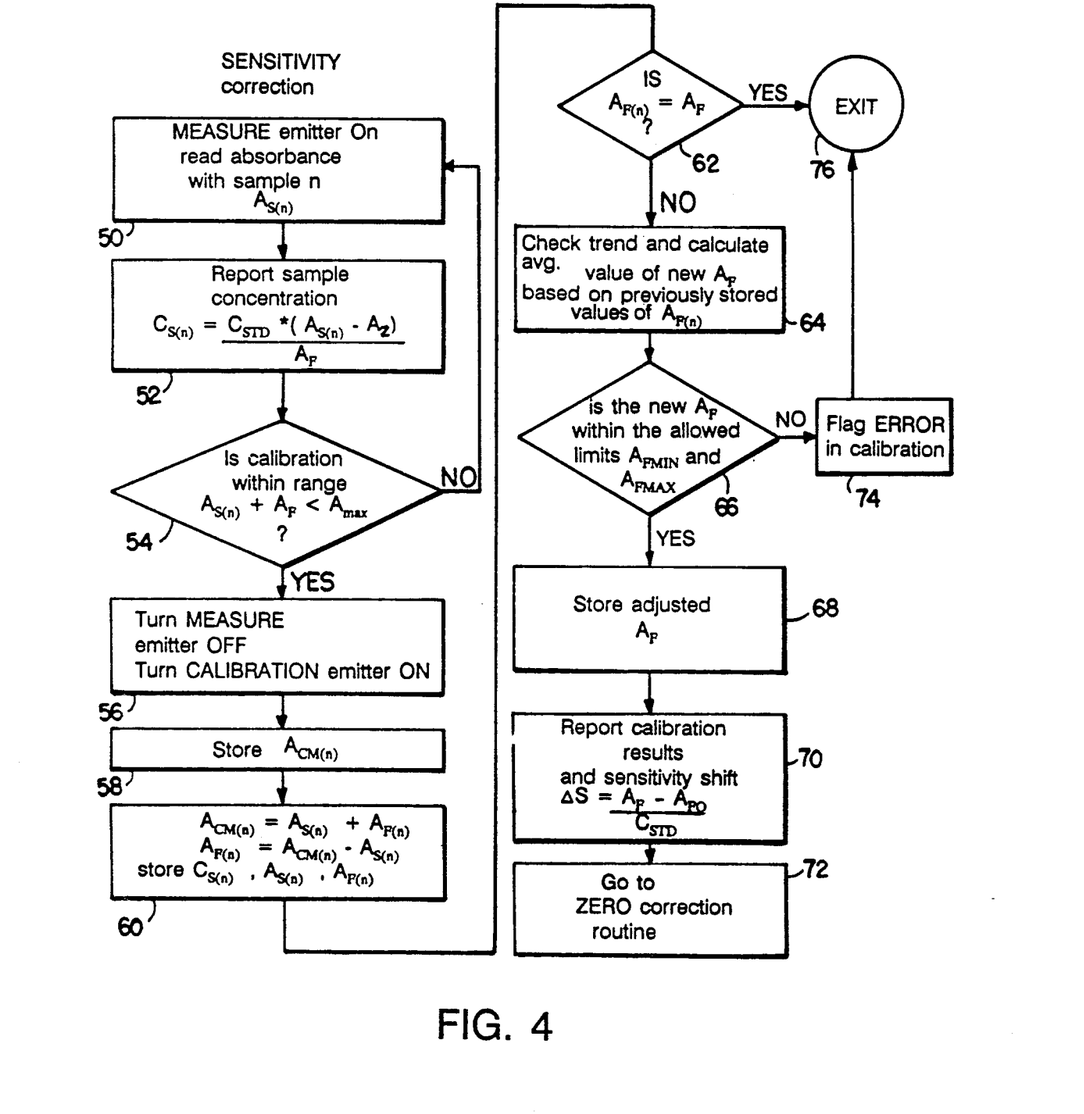
FIG. 4 is a flowchart illustrating a sensitivity correction routine for the embodiment of FIG. 1.

The routine implemented by the instrument in a normal measurement operation is shown in the first two blocks of FIG. 4.

The second operation, the "calibration" operation is performed with the sample 18 in place and may be performed for all measurements or at selected intervals. In this step, the central processing unit causes the calibration lamp 4 to illuminate while the sample lamp remains deenergized. The calibration lamp emits polychromatic light that passes through the calibration filter 10. The calibration filter absorbs light at the measurement wavelength to a degree which is precisely known, e.g. 30 percent of the measurement range. It may also absorb some energy at the reference wavelength; this should be significantly less than the degree to which the measurement wavelength is absorbed.

Unabsorbed light from the calibration filter 10 passes into the first fiber optics bundle 14 and on through the sample cell where portions of it are absorbed by constituents of the sample being monitored. Unabsorbed portions of the light then pass into the second fiber optics bundle 16 and spectral portions are detected and corresponding values are provided to the central processing unit in the manner as they were in the measure operation.

Figure 3:
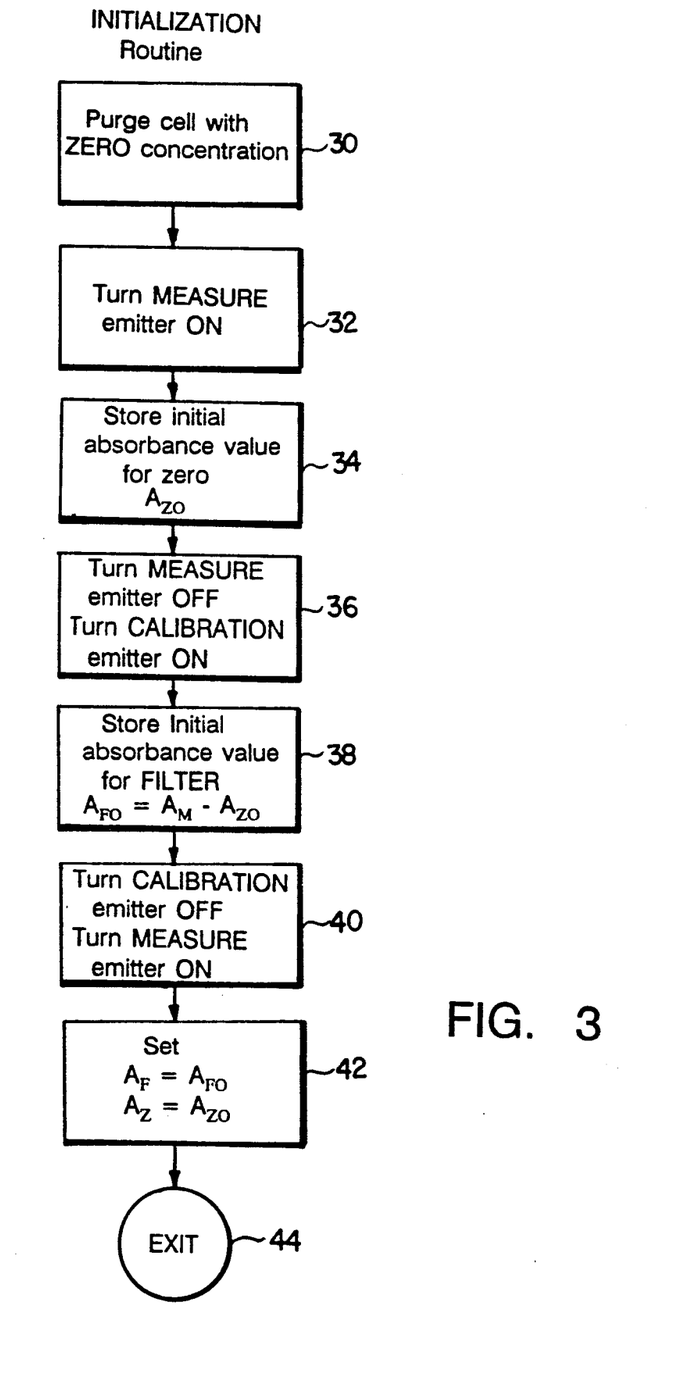
FIG. 3 is a flowchart illustrating an initialization routine for the embodiment of FIG. 1.
Figure 5:
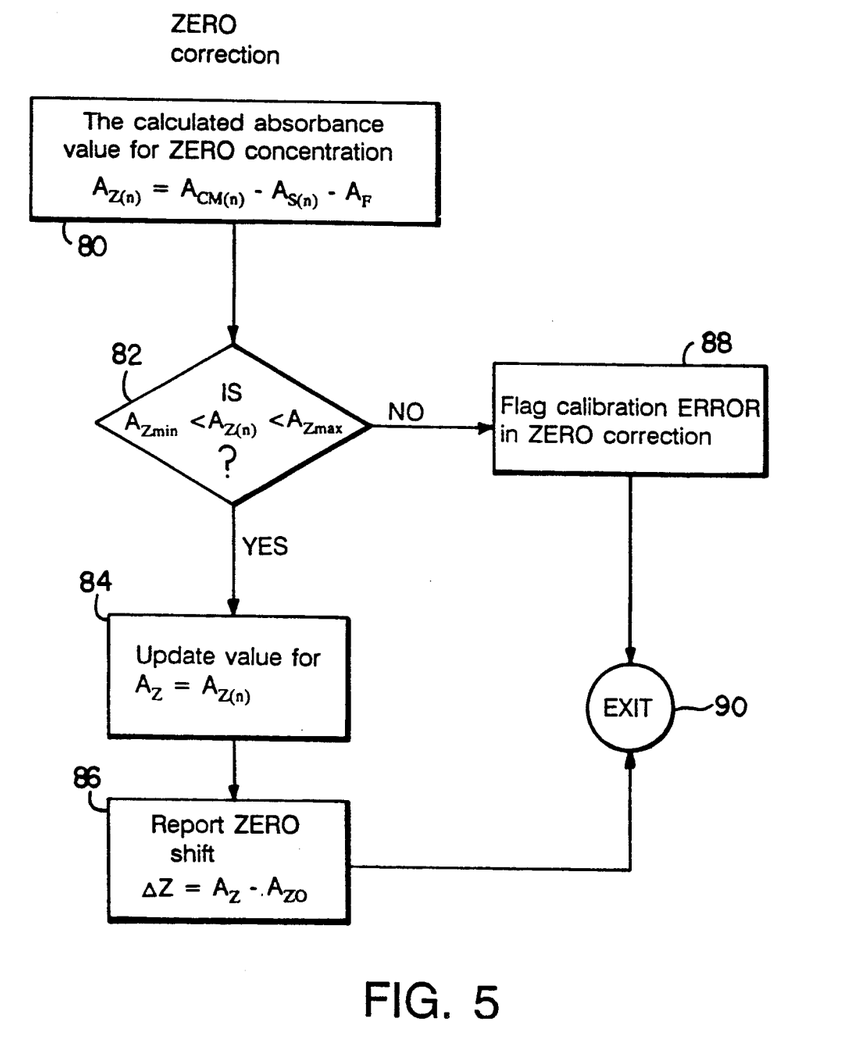
FIG. 5 is a flowchart illustrating a zero correction routine for the embodiment of FIG. 1.

The central processing unit divides the digitized measure value by its corresponding reference value and takes the logarithm of the result to generate an absorbance value for each measurement. This "calibration" reading is used in subsequent calibration calculations, as described below in connection with FIGS. 3–5. Basically, a prior "measure" reading and a "calibration" reading, both taken with the same fluid sample present, are effectively compared to remove the effect of the fluid sample from the "calibration" reading. Then the residual value is effectively compared to the known, i.e.

previously determined, actual absorbance of the calibration filter. From this, or a series of such measurements, a calibration adjustment can be determined, or equivalently, a report may be generated as to the degree to which the instrument was drifted from the initial state.

The values given in FIGS. 3-5 are defined as follows:
$A_F$—FILTER absorbance value used in calculations
$A_{FO}$—Initial absorbance value for FILTER
$A_{F(n)}$—Calculated absorbance value of FILTER with nth sample in situ
$A_{Fmin}$—Minimum limit for FILTER absorbance value
$A_{Fmax}$—Maximum limit for FILTER absorbance value
$A_{CM(n)}$—Absorbance value of nth sample with CALIBRATION emitter
$A_M$—Absorbance measured
$A_{max}$—Maximum limit for measured absorbances
$A_{S(n)}$—Absorbance value with nth sample in situ
$A_Z$—ZERO absorbance value used in calculations
$A_{Z0}$—Initial absorbance value for ZERO concentration
$A_{Z(n)}$—Calculated absorbance value for ZERO with nth sample in situ
$A_{Z(n)}$—Minimum limit for ZERO absorbance value
$A_{Z(n)}$—Maximum limit for ZERO absorbance value
$C_{S(n)}$—Calculated nth sample concentration
$C_{STD}$—Concentration value corresponding to FILTER selected (Value entered by operator)

When the instrument is first turned on, the central processing unit performs an initialization routine, as shown in FIG. 3. This initialization routine is performed 30 on an empty cell 12 or a cell filled with "zero" sample (sample containing "zero" concentration of the component of interest, e.g., for color in liquids, distilled water is used as a "zero" sample) in order to obtain an initial zero value for the instrument. Thus an initial "measure" operation is performed by turning the measure lamp on 32, calculating and storing the resulting absorbance value for zero sample present ($A_{Z0}$) 34 and turning the measure lamp off 36.

Likewise, an initial "calibration" operation for the filter is performed by turning the calibration lamp on 36 and performing a further measure operation with the circuitry to obtain an absorbance measurement, $A_M$. The initial measured absorbance value of the calibration filter $A_{FO}$, is then obtained by subtracting the absorbance value for zero $A_{Z0}$ from the measured absorbance $A_M$, this value $A_{FO}$ then being stored.

Now, with the calibration lamp off 40, and the measure emitter on, a further measurement 40 is performed, the zero values $A_{FO}$ and $A_{Z0}$ are respectively stored as the filter and absorbance values $A_F$ and $A_Z$ to be used in further calculations, and using these values the zero value of the scale reading instrument is set. Here the known absorption value of the calibration filter, i.e. the concentration level of the compound of interest that it represents, is used to standardize the readings of the instrument. This completes the initialization routine 44.

Once the initialization routine is complete, the instrument may be used to perform absorbance measurements, and to display these values on the display 24 or otherwise present them to the user or another piece of equipment. These values may be expressed to the user as concentration values. After a certain period, which is user-definable, the instrument performs a self calibration.

Figure 6:
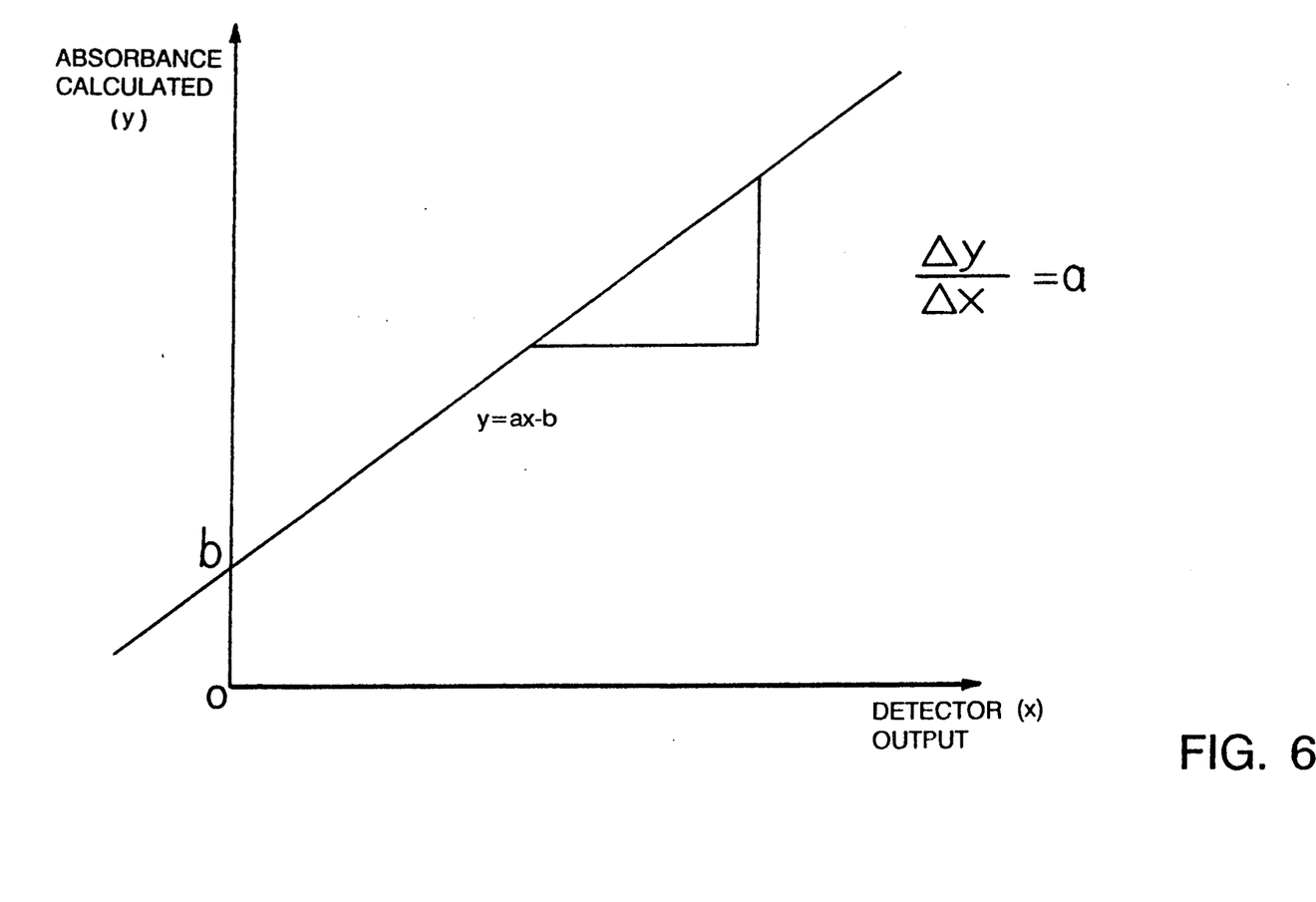
FIG. 6 is an idealized response plot for the instrument of the invention.

The self calibration routine, which is shown in flow diagram in FIGS. 4 and 5, includes a sensitivity correction routine that is used to adjust the sensitivity of the instrument and a zero correction routine that adjusts the zero value of the instrument. As may be seen in FIG. 6, a sensitivity change corresponds to a change in the gain of the instrument or $\Delta y/\Delta x$, while a change in zero value corresponds to a change in the zero intercept b of the instrument.

The sensitivity correction routine (FIG. 4) begins with a measure operation 50 that reads the absorbance $A_{S(n)}$ for sample n. The central processing unit calculates a corresponding sample concentration value using the formula shown at step 52 of FIG. 4 and displays it.

The self calibration routine then determines whether the calibration is within range by determining if the absorbance value measured for the current sample $A_{S(n)}$ added to the current filter value used in calculations $A_F$ is within the range of measurement of the system 54. If it is not, it is probable that the operating range for the automatic calibration has been exceeded. In this case, calibration can not take place, and the central processor unit flags this condition to the user.

If the unit can be calibrated, the central processing unit turns off the measure lamp and turns on the calibration lamp 56 to obtain and store 58 an absorbance value for the sample and the filter together. From this value, the central processing unit computes a calculated absorbance value for the filter $A_{F(n)}$ 60. If this absorbance value is the same $A_F$ that currently is used 62, the system is properly calibrated, and the calibration routine is complete 76.

If the measured absorbance value of the calibration filter is different, then it is known that the instrument has drifted since the actual absorbance of the calibration filter itself is a known, fixed quantity. To correct for this instrument drift, the central processing unit generates a new current filter absorbance value $A_F$, 64, taking into consideration past trends of the value. The new value will be determined by the average of a set of most recent values, unless there is an appreciable trend in one direction or the other, which might be caused by a system malfunction, for example, component failure.

The central processing unit then tests the new filter absorbance value to see if it is within the allowed range 60. If it is outside the range, the instrument displays an error indication 74 and ceases its attempt at calibration 76. If the new, adjusted, filter absorbance value $A_F$ is within the proper range, it is stored for further use.

The central processing unit then reports to the user a sensitivity value $\Delta S$ that indicates to the user that the calibration has shifted. This value is obtained from the equation in block 70 of FIG. 4. By comparison of the value of new and previous determinations of $A_F$, the performance history of the sensitivity of the instrument can be determined and reported. Execution of the "calibration" operation proceeds 72 to the zero correction routine.

The zero correction routine, which is shown in flow diagram in FIG. 5, generates a zero value for use in further measurements. This routine begins with a calculation of a zero value computed by subtracting the current filter absorption value $A_F$ and the current measured sample absorbance $A_{S(n)}$ from the measured absorbance of the filter and sample together $A_{CM(n)}$ for the current sample 80. If this value is determined to be within an acceptable range of zero absorbance values, the current zero value is updated 84, the zero shift is reported to the operator 86, and the calibration routine is completed 90. If the value is outside of the acceptable range, an error condition is flagged 88.

Once the calibration routines are completed, the instrument is ready to perform further measurements, until it is recalibrated again. The above method may thus repetitively recalibrate the instrument by simply performing successive updates of the $A_F$ variable.

Figure 7:
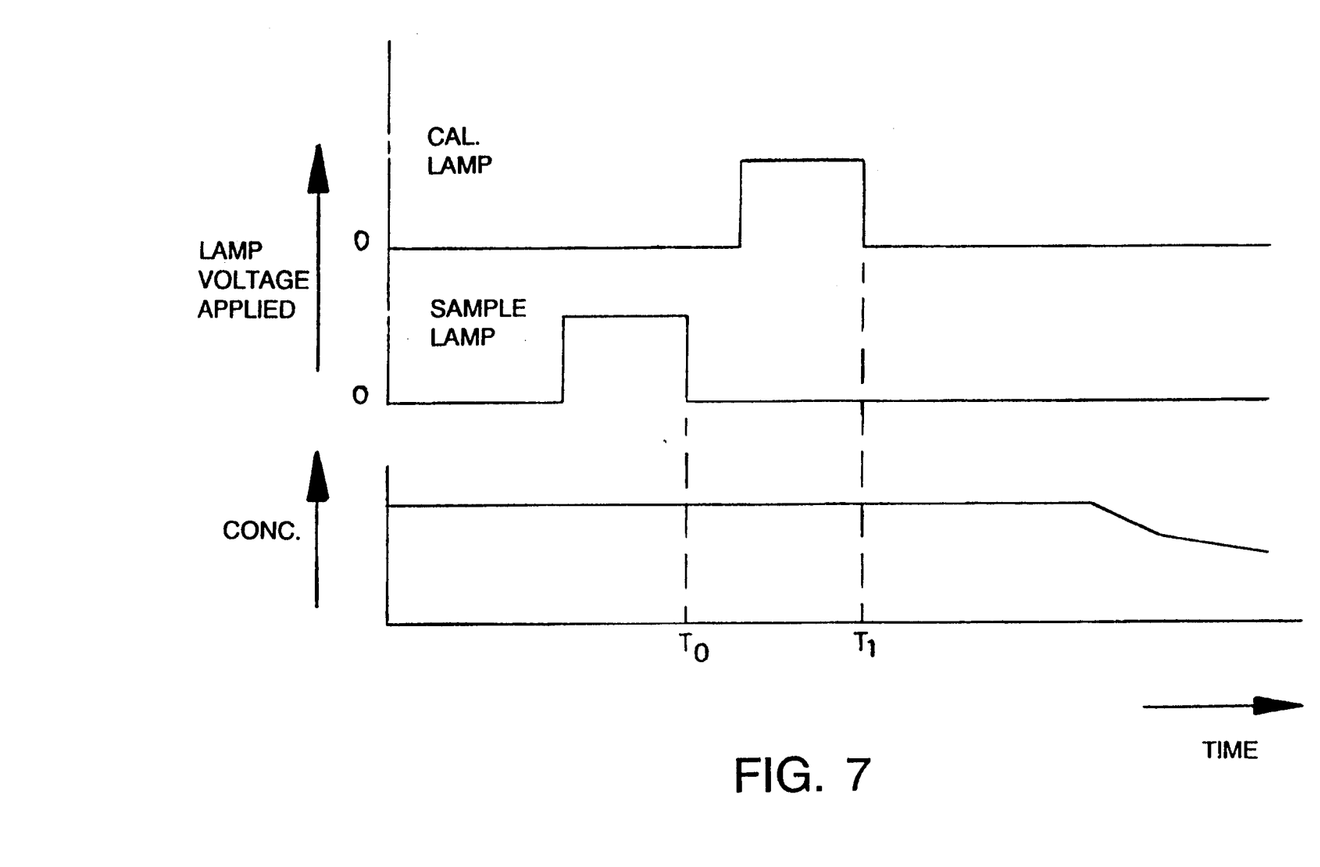
FIG. 7 is a set of graphs showing the voltage applied to the sample and calibration lamps and the concentration of the sample against time for a single calibration operation.

It will be observed that one assumption inherent in the above discussion in respect of in-line operation, is that the flow of fluid must have an absorbance that is substantially constant during a measure operation and the following calibration operation (i.e., its characteristic maximum rate of change is small), or the calibration may be performed incorrectly. This is illustrated in FIG. 7, where it can be seen that between the measurement points $T_0$ and $T_1$ when the detector measures unabsorbed light, the concentration of the solution must remain stable. It is found in practice that the time interval for making such measurements is sufficiently short that concentrations in many processes to be monitored do not vary significantly, so that valid readings in-line can be obtained.

For on-line analysis, i.e. when a sample is captured and retained in the sample cell, the same sample remains in the cell for both "measure" and "calibration" operations so that this is of no concern.

Figure 8:
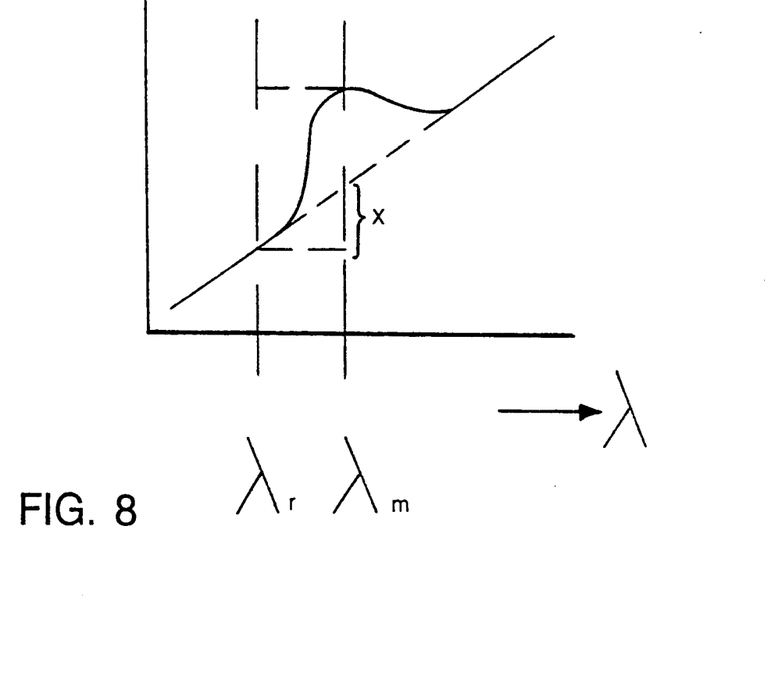
FIG. 8 is a plot of absorbance against wavelength for a measurement situation where the baseline absorption is sloping.
Figure 9:
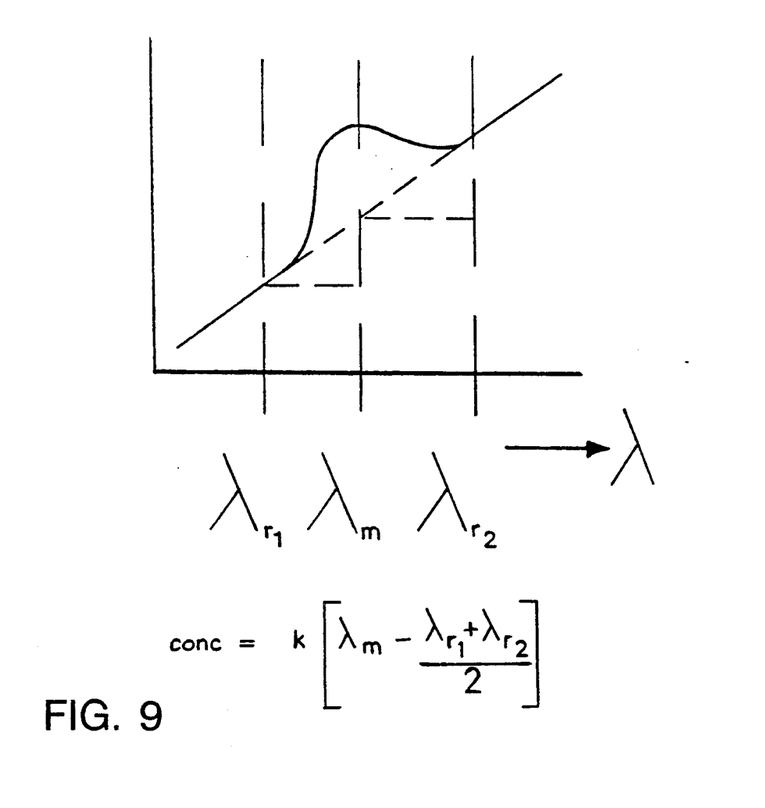
FIG. 9 is a plot of absorbance against wavelength for a measurement situation where the baseline absorption is sloping, showing two reference wavelengths.

In some cases, constituents of the sample may cause the baseline absorption around the wavelength of interest to be skewed by an amount X, as shown in FIG. 8. This can cause the reference value to depend on the concentration of constituents that are not important to the measurement and thus affect the accuracy of measurements. In this situation, two or more reference detectors may be used, and their average value used to determine the effective reference value, as illustrated in FIG. 9.

By use of the instrument as described, the calibration of the instrument of FIG. 1 can be automatically checked and corrected during continuing operations without evacuating the sample or using any test samples. The system also contains no moving parts which contributes to compactness as well as to reliability and less need for maintenance. This instrument, therefore, is particularly well suited for use in rugged field applications such as waste water monitoring where dependable operation without the need for regular support by highly qualified technicians is important.

Furthermore, this optical apparatus and associated method are equally useful for measurements in the visible, infrared and ultra-violet regions of the spectrum, when supplied with the appropriate emitters, filters, and detectors.

In certain instances, it may be useful to replace the two lamps with a single source and a shutter mechanism or its equivalent thereby allowing the same source to illuminate the sample via the sample and filter paths. This requires the addition of a moving part that can be less reliable or more expensive, but may be warranted in certain situations. For example, when using an arc source or other embodiment in which the emitted radiant energy from the emitter source is optimized at its maximum, a single emitter and suitable means for switching between from an optical path with and without the calibration filter present can be employed.

Numerous other instruments may be manufactured to measure absorbance or other physical parameters using the calibration method of the invention.

Figure 10:
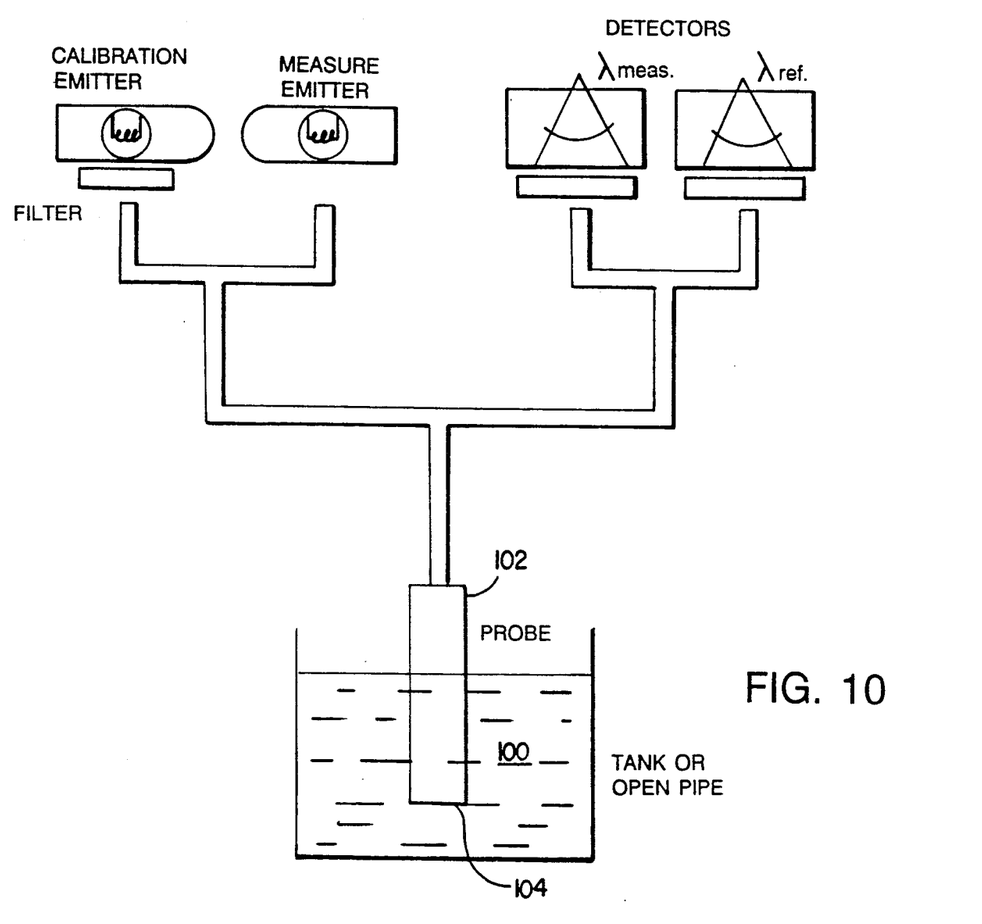
FIG. 10 is a schematic illustration of a colorimeter embodiment.

For example, FIG. 10 shows a probe-based configuration suitable for use as a titrometer or a colorimeter. This instrument operates in much the same way as the spectrophotometer embodiment, with the exception that the light passes through the sample fluid 100 in the probe 102 and is reflected off of a reflecting surface 104 back through the probe before the resulting absorbance is measured. The sampling technique of the above-mentioned patent may be employed to especial advantage, or other techniques may be used.

Figure 11:
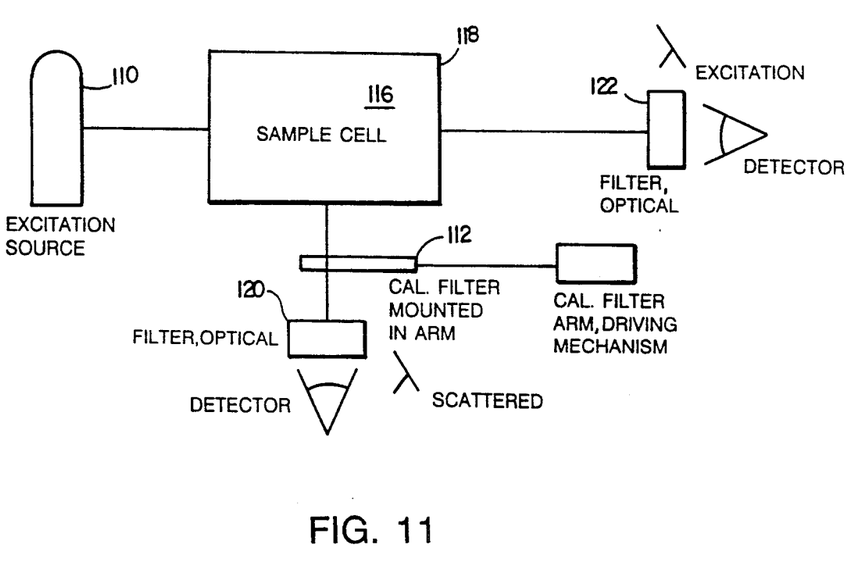
FIG. 11 is a schematic illustration of an embodiment of the invention that measures concentration by detecting scattering effects within the sample.

An instrument for measuring concentration by detecting scattered radiation is shown in FIG. 11. This instrument includes an emitter, such as an ultraviolet arc source 110 that may emit light into a sample cell 118 and excite the sample 116 and cause a certain degree of scattering. Detectors directly opposite the incident path 122 of the exciting radiation and at right angles thereto 120 measure transmitted and scattered radiation, respectively. The ratio of the amplitude of detected scattered radiation and the transmitted scattered radiation is proportional to the concentration of the material being measured.

In this instrument, the calibration filter 112 of known absorbance that is translated into and out of the optical path of the detector provides the ability to perform alternate "measure" operations and "calibration" operations. This instrument may be calibrated in essentially the same way as the dual lamp spectrophotometer of FIG. 1. The basis structure of this embodiment is thus applicable to scattering effects such as Raleigh scattering and to fluorescence measurements.

Figure 12:
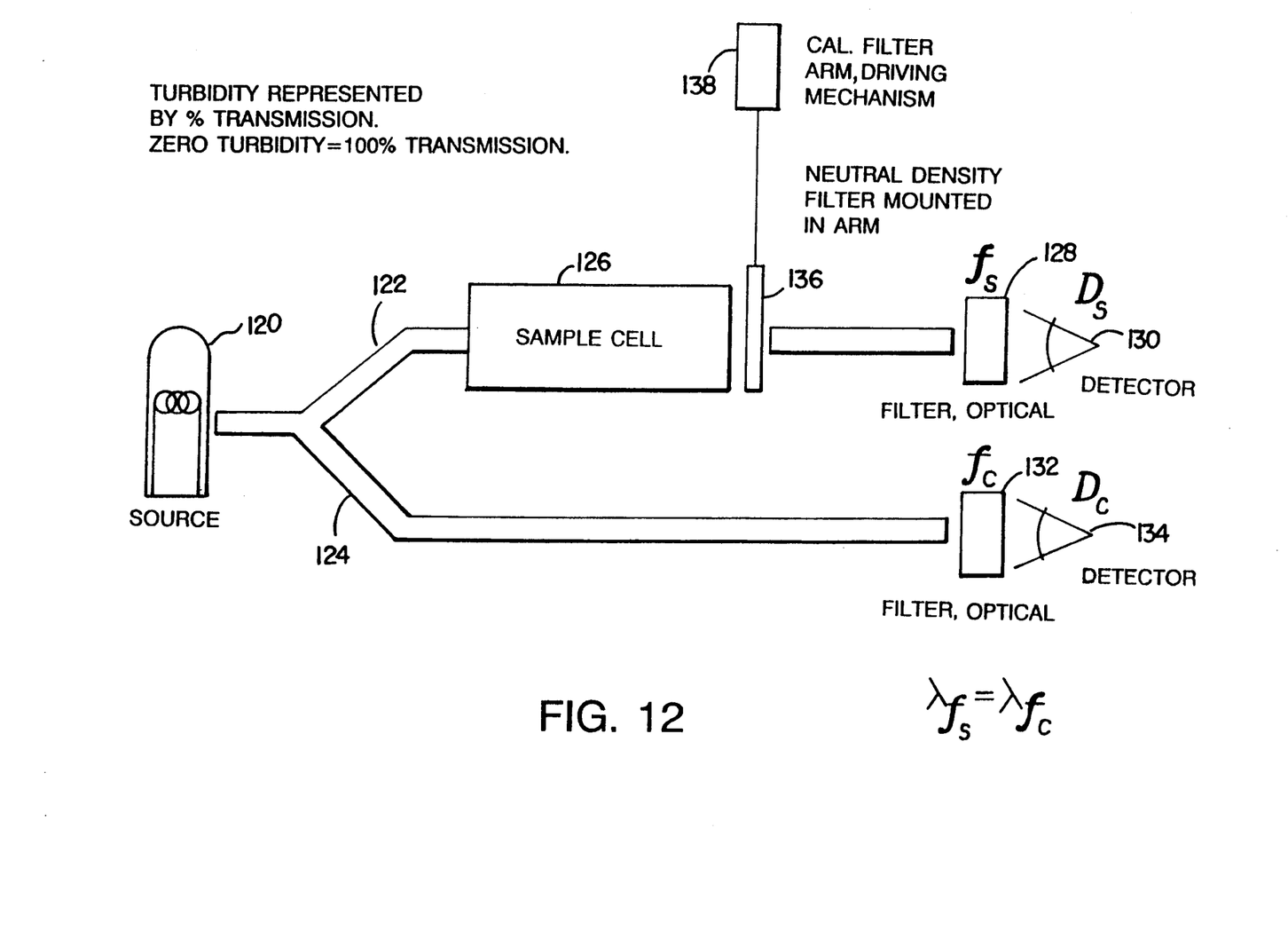
FIG. 12 is a schematic illustration of a turbidimeter embodiment.

Referring to FIG. 12, a turbidimeter embodiment includes a source 120 that provides optical radiation along two optical paths 122, 124. The sample path brings a portion of the radiation through a sample cell 126 and a sample filter 128 to a sample detector 130. The reference path brings a portion of the radiation through a reference filter 132 to a reference detector. A calibration filter driving mechanism 138 may translate a neutral density calibration filter 136 of known absorbance into and out of the optical path in series with the sample cell.

The ratio of the received radiation energy at the sample detector to that received at the reference detector is related to the transmission through the sample. Higher values of transmission are indicated as lower values of turbidity and vice-versa. The neutral density calibration filter, of known absorbance, provides the ability to perform measure operations and calibration operations. This instrument may therefore be calibrated in much the same way as the dual lamp spectrophotometer.

In the embodiments shown, stored measurements are used to effectively adjust the instrument performance. In other embodiments, calibration errors kept in memory without updating working values, and the instrument performance may readily be revised and used, e.g. by computer using the raw instrument data for measure and calibration readings together with stored values representing an initialized condition of the instrument.

Other embodiments are within the scope of the following claims.

What is claimed is:

1. An optical analytical instrument for quantitative measurements capable of producing amplitude readings based upon the effect of a fluid upon a selected fixed wavelength in a beam of optical radiation to determine a quantitative physical parameter of the fluid, said instrument comprising a source of suitable optical radiation, a detector means responsive to said selected fixed wavelength within a predetermined amplitude measurement range of the instrument, means defining a zone for said fluid, means defining an optical path from said radiation source through said fluid zone to said detector means, reading and control circuitry for taking from said detector means at least two amplitude readings of optical energy of said selected fixed wavelength that result from the influence of the fluid on said optical radiation without there having occurred substantial change to the fluid, means during one of said readings for including in said optical path a filter of known absorbance that absorbs a predetermined portion of the energy at said fixed wavelength, said portion representing a substantial fraction of said amplitude measurement range of the instrument so that the respective reading represents an amplitude calibration reading within said measurement range of the instrument, calibration-value-determining means operable while a sample of said fluid remains unchanged in said fluid zone, first to compare, effectively, said two amplitude readings at said selected fixed wavelength to remove said effect of said fluid from the value of said calibration reading, second, to compare, effectively the residual value of said calibration reading to a known value based on the known absorbance of said filter, and, third, on the basis of said second comparison, to determine an amplitude calibration value for said instrument based on amplitude values derived while said fluid sample remains unchanged in said fluid zone.

2. An optical analytical instrument capable of producing readings based upon the effect of a fluid upon a beam of optical energy to determine a physical parameter of the fluid, said instrument comprising a source of suitable optical radiation, a detector means, means defining a zone for said fluid, means defining an optical path from said radiation source through said fluid zone to said detector means, reading and control circuit for taking from said detector means at least two readings of optical energy that has been influenced by the fluid without there having occurred substantial change to the fluid, means during one of said readings for including in said optical path a filter of known absorbance so that the respective reading represents a calibration reading, calibration-value-determining means constructed first to compare, effectively, said two readings to remove said effect of said fluid from the value of said calibration reading, second, to compare, effectively the residual value of said calibration reading to a known value based on the known absorbance of said filter, and, third, on the basis of said second comparison, to make a calibration adjustment based on values derived while said fluid sample remained unchanged in said fluid zone, wherein said optical radiation source comprises two separately energizable radiation emitters, said optical path from said source having two branches, one defining a respective optical path from each radiation emitter, with both branches transmitting via a substantially common path through said sample, one of said emitters, denoted the "measure" emitter, energized by said control means during the taking of a normal measurement reading and the other emitter, denoted the "calibration" emitter, energized by said control means during the taking of a calibration reading, said filter of known absorbance being included in the optical path from said calibration emitter to said fluid zone.

3. An optical analytical instrument capable of producing readings based upon the effect of a fluid upon a beam of optical energy to determine a physical parameter of the fluid, said instrument comprising a source of suitable optical radiation, a detector means, means defining a zone for said fluid, means defining an optical path from said radiation source through said fluid zone to said detector means, reading and control circuitry for taking from said detector means at least two readings of optical energy that has been influenced by the fluid without there having occurred substantial change to the fluid, means during one of said readings for including in said optical path a filter of known absorbance so that the respective reading represents a calibration reading, calibration-value-determining means constructed first to compare, effectively, said two readings to remove said effect of said fluid from the value of said calibration reading, second, to compare, effectively the residual vale of said calibration reading to a known value based on the known absorbance of said filter, and, third, on the basis of said second comparison, to make a calibration adjustment based on values derived while said fluid sample remained unchanged in said fluid zone, wherein said optical radiation source comprises two separately energizable radiation emitters, said optical path from said source having two branches, one defining a respective optical path from each radiation emitter, with both branches transmitting via a substantially common path through said sample, one of said emitters, denoted the "measure" emitter, energized by said control means during the taking of a normal measurement reading and the other emitter, denoted the "calibration" emitter, energized by said control means during the taking of a calibration reading, said filter of known absorbance being included in the optical path from said calibration emitter to said fluid zone, and wherein said instrument has no moving parts for accomplishing calibration, said control means constructed and arranged such that normal and calibration readings for use by said instrument in establishing said calibration adjustment are effected by selective energization of said emitters during operation.

4. The optical analytical instrument of claim 1, 2 or 3 in the form of an in-line analytical instrument in which said means defining said fluid zone comprises a conduit for at least part of a process stream through which process fluid flows, said process stream having a characteristic maximum rate at which said parameter can change, and said reading and control means constructed, in relation to said process stream, to take said two readings within such a short time interval that there is insufficient passage of time to allow substantial change to occur in said parameter of said fluid in said process stream.

5. The optical analytical instrument of claim 1, 2 or 3 in the form of a titration chamber constructed to be filled by a liquid process stream and, after titration, flushed only by the process stream.

6. The optical analytical instrument of claim 1, 2 or 3 in the form of a titration chamber constructed to receive a known repeatatable small sample of process stream liquid and after titration said chamber is constructed to be flushed with a suitable liquid.

7. The optical analytical instrument of claim 5 in the form of a colorimeter.

8. The optical analytical instrument of claim 1, 2 or 3 in the form of a colorimeter, the portion of said optical path in said fluid zone being defined by a probe which includes a reflector whereby energy which enters said fluid zone is reflected to pass back through said fluid zone to said detector means.

9. The optical analytical instrument of claim 1, 2 or 3 in the form of an absorption spectrophotometer, said detector means comprising at least two detectors sensitized to respectively different wavelengths, one wavelength corresponding to a characteristic absorption of a component of interest in said fluid zone, the detected signal varying with the concentration of said component, and the other wavelength being a reference wavelength for which said component of interest has relatively low absorbance.

10. The optical analytical instrument of claim 1 or 2 wherein said detector means is positioned to receive scattered or fluorescent radiant energy from said sample.

11. The optical analytical instrument of claim 10 wherein said filter is positioned to filter said scattered or fluorescent radiant energy.

12. The optical analytical insturment of claim 10 wherein said detector is postioned to receive Raleigh scattering or fluorescence.

13. The optical analytical instrument of claim 1 in the form of a turbidimeter.

14. The optical analytical instrument of claim 13 further including an optical reference path bypassing said sample.

15. The optical analytical instrument of claim 1, 2 or 3 wherein said means defining said optical path from said radiation source to said fluid zone is comprised of optical fibers.

16. The optical analytical instrument of claim 1, 2 or 3 wherein said means to make a calibration adjustment is constructed to calibrate the instrument.

17. The optical analytical instrument of claim 16 wherein said means responsive to make said calibration adjustment comprises means to adjust the sensitivity of the instrument.

18. The optical analytical instrument of claim 16 wherein said means to make said calibration adjustment comprises means to adjust the zero reference of said instrument.

19. The optical analytical instrument of claim 1, 2 or 3 including means to provide said known value in the form of means to store a reading of the detector means taken with said filter of known absorbance in place and with said fluid zone empty.

20. The optical analytical instrument of claim 6 in the form of a colorimeter.

21. The optical analytical instrument of claim 1 wherein said substantial fraction is of the order of 30 percent.

22. The optical analytical instrument of claim 1 wherein said instrument has no moving parts for accomplishing calibration.

23. A method of calibrating an optical analytical instrument capable of producing amplitude readings based upon the effect of a fluid upon a selected fixed wavelength in a beam of optical radiation to determine a quantitative physical parameter of the fluid, comprising taking from a detector means responsive to said selected fixed wavelength at least two amplitude readings at said selected fixed wavelength and within a predetermined amplitude measurement range of the instrument, of optical energy that result from the influence of the fluid on the optical radiation in a fluid zone without there having occurred substantial change to the fluid, including in said optical path a filter of known absorbance that absorbs a predetermined portion of the energy at said fixed wavelength that represents a substantial fraction of said amplitude measurement range of the instrument so that one of said amplitude readings represents a calibration reading within said measurement range of the instrument, first, comparing, effectively, said two amplitude readings to remove said effect of said fluid from the value of said calibration reading, second, comparing, effectively, the residual value of said calibration reading to a known value based on the known absorbance of said filter, and, on the basis of said second comparison, determining an amplitude calibration value for the instrument based on values derived while said fluid sample remains unchanged in said fluid zone.

24. A method of calibrating an optical analytical instrument capable of producing readings based upon the effect of a fluid on a beam of optical energy to determine a physical parameter of the fluid, wherein said optical radiation source comprises two separately energizable radiation emitters, comprising taking from a detector means at least two readings of optical energy that has been influenced by the fluid in a fluid zone without there having occurred substantial change to the fluid, energizing a "measure" emitter by said control means during the taking of a normal measurement, energizing a "calibration" emitter, by said control means during the taking of a calibration reading while said filter of known absorbance is included in the optical path from said calibration emitter to said fluid, first, comparing, effectively, said two readings to remove said effect of said fluid from the value of said calibration reading, second, comparing, effectively, the residual value of said calibration reading to a known value based on the known absorbance of said filter, and, on the basis of said second comparison, making a calibration adjustment based on values derived while said fluid sample remained unchanged in said fluid zone.

25. A method of calibrating an optical analytical instrument capable of producing readings based upon the effect of a fluid on a beam of optical energy to determine a physical parameter of the fluid, wherein said optical radiation source comprises two separately energizable radiation emitters, comprising taking from a detector means at least two readings of optical energy that has been influenced by the fluid in a fluid zone without there having occurred substantial change to the fluid, energizing a "measure" emitter by said control means during the taking of a normal measurement, energizing a "calibration" emitter, by said control means during the taking of a calibration reading while said filter of known absorbance is included in the optical path from said calibration emitter to said fluid, first, comparing, effectively, said two readings to remove said effect of said fluid from the value of said calibration reading, second, comparing, effectively, the residual value of said calibration reading to a known value based on the known absorbance of said filter, and, on the basis of said second comparison, making a calibration adjustment based on values derived while said fluid sample remained unchanged in said fluid zone, wherein said calibration adjustment is effected by selective energization of said emitters during operation without moving any parts of said instrument.

26. The method of claim 23, 24 or 25 wherein said fluid flows in a process stream further comprising taking two readings by said control means within such a short time interval that there is insufficient passage of time to allow substantial change to occur in said parameter of said fluid in said process stream.

27. The method of claim 23, 24 or 25 further including the steps of filling a titration chamber by a liquid process stream and, after titration, flushing said titration chamber only by the process stream.

28. The method of claim 23, 24 or 25 further including the steps of filling a titration chamber by a liquid process stream and, after titration, flushing said titration chamber by a suitable liquid.

29. The method of claim 27 wherein the calibration is performed for a colorimeter.

30. The method of claim 23, 24 or 25 wherein the calibration is performed for an absorption spectrophotometer.

31. The method of claim 23, 24 or 25 wherein the calibration is performed for an instrument responsive to Raleigh scattering or fluorescence.

32. The method of claim 23, 24 or 25 wherein the calibration is performed for a turbidimeter.

33. The method of claim 23, 24 or 25 wherein said step of making a calibration adjustment calibrates the instrument.

34. The method of claim 33 wherein said calibration adjusts the sensitivity of the instrument.

35. The method of claim 33 wherein said calibration adjusts the zero reference of the instrument.

36. The method of claim 23, 24 or 25 further including the step of storing a reading of the detector means taken with said filter of known absorbance in place and with said fluid zone empty.

37. The method of claim 23, 24 or 25 wherein said step of making a calibration adjustment includes updating a current filter absorbance value.

38. The method of claim 37 wherein said calibration adjustment step is periodically repeated and said current filter value is successively updated during these repetitions.

39. The method of claim 37 wherein past trends in said current absorbance value are taken into consideration in updating said current absorbance value.

40. The apparatus of claim 1 or the method of claim 23 wherein, respectively, the instrument is constructed or the method is conducted to measure concentration or the like, C, according substantially to the relationship $$C_{s(n)} = \frac{C_{std} \times (A_{s(n)} - A_z)}{A_F}$$

in which the values are substantially as defined in the foregoing specification.

41. The method of claim 28 wherein the calibration is performed for a colorimeter.

42. The method of claim 23 wherein said substantial fraction is of the order of 30 percent.

43. The method of claim 23 wherein said calibration adjustment is effected without moving any parts of said instrument.

* * * * *